(12) United States Patent
Klitmose et al.

(10) Patent No.: US 6,277,098 B1
(45) Date of Patent: *Aug. 21, 2001

(54) INJECTION DEVICE WITH ELECTRONIC PRESENTATION OF SET DOSES

(75) Inventors: Lars Peter Klitmose, Gentofte; Henrik Egesborg Hansen, Hellerup, both of (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/981,772
(22) PCT Filed: Mar. 3, 1997
(86) PCT No.: PCT/DK97/00093
  § 371 Date: Dec. 8, 1997
  § 102(e) Date: Dec. 8, 1997
(87) PCT Pub. No.: WO97/33638
  PCT Pub. Date: Sep. 18, 1997

(30) Foreign Application Priority Data

Mar. 12, 1996 (DK) .................................................... 0285/96
Nov. 11, 1996 (DK) .................................................... 1264/96

(51) Int. Cl.⁷ ...................................................... A61M 5/00
(52) U.S. Cl. ............................ 604/207; 604/65; 604/187
(58) Field of Search ................................... 604/201, 207, 604/19, 500, 48, 65, 130, 131, 140, 150, 151, 187

(56) References Cited

U.S. PATENT DOCUMENTS

| | | |
|---|---|---|
| 4,529,401 | 7/1985 | Leslie et al. . |
| 4,908,017 | 3/1990 | Howson et al. . |
| 5,254,096 | 10/1993 | Rondelet et al. . |
| 5,697,916 | * 12/1997 | Schraga ................................ 604/201 |
| 5,728,074 | * 3/1998 | Castellano et al. .................. 604/207 |

FOREIGN PATENT DOCUMENTS

WO 84/01719    5/1984   (WO) .

* cited by examiner

Primary Examiner—Richard K. Seidel
Assistant Examiner—Cris L. Rodriguez
(74) Attorney, Agent, or Firm—Skadden, Arps, Slate, Meagher & Flom LLP

(57) ABSTRACT

An injection device has signal generators (11, 12, 13, 14) which are connected to operative elements (8, 3, 5, 4) of the device and which give off signals which represents the operative condition of the device. The signals are sent to an electronic circuit which controls a presentation of the operational condition of the device and presents operational conditions, which are defined as not allowed, as error indications by switching off the display presenting the operational condition of the device. The number of signals from each generator is counted and a number of operations exceeding a pre-set number for the signal generator in question is interpreted as representing a not allowed operational condition.

17 Claims, 2 Drawing Sheets

INJECTION DEVICE WITH ELECTRONIC PRESENTATION OF SET DOSES

CROSS-REFERENCE TO RELATED APPLICATIONS

Figure 1:
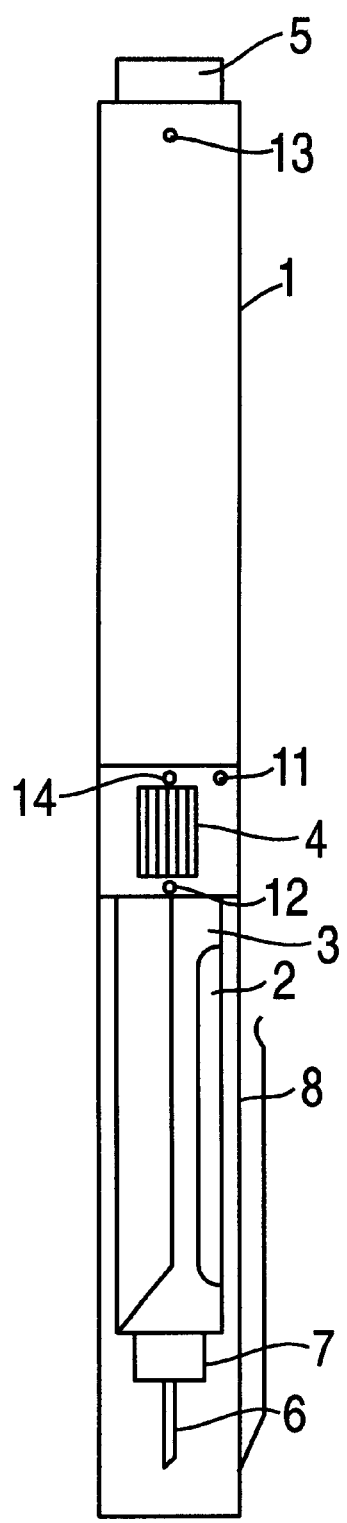

This application is a 35 U.S.C. 371 national application of PCT/DK97/00093 filed Mar. 3, 1997 and claims priority under 35 U.S.C. 119 of Danish applications 0285/96 filed Mar. 12, 1996 and 1264/96 filed Nov. 11, 1996, the contents of which are filly incorporated herein by reference.

The invention relates to injection devices for the injection of set doses of a medicine, the operational condition of the device being electronically presented by a circuit which receives a pattern of input signals from signal generators connected to the operative elements of the device.

Such an injection device may have the shape of a device comprising a dose setting wheel and an injection button and a protective cap covering at least a needle receiving part of the device and possibly the dose setting wheel. The electronic presentation usually has the shape of a electronic display, but also a speech circuit may be used which in speech summarize the condition of the device. Also an electro-mechanical device presenting a tactile resume may be imagined.

The generators connected to the operative elements of the device may be switches switching on and off a current or they may be active current generators. Generators of the switch type may be connected to the protective cap or the injection push button to indicate one of two alternative positions, i.e. the cap on or the cap off, or the push button projecting or pressed home.

A generator of an active type which itself produces a current when activated may be connected to the dose setting wheel to provide current signals reflecting the turning of this wheel, e.g. a pulse per unit set by turning the wheel and the pulse having a polarity indicating whether the dose setting is increased or decreased by turning of the wheel. The dose setting signals may also be provided by operating a number of switches.

The use of electronic presentation of the device parameters makes it possible to use a display with large digits as opposed to mechanical displays by which the movements of the dose setting wheel and a plunger operating a piston in an ampoule with the medicine to be injected set narrow limits on the size of the displayed digits.

The electronic presentation depends on electric switches and generators which may, e.g. due to wear, fail without warning and cause a false electric signal and consequently a false displaying. But, mechanical wear may or may not reveal itself.

Consequently it is an object of the invention to provide a device by which unreliable electrical or mechanical components are detected before they cause a wrong dosing of the medicine injected by the device.

This may be obtained by a device as the one described in the opening paragraph of this specification, which device is characterized in that it comprises a circuit which receives input signals from signal generators connected to operative elements of the device and gives off a signal which represents the operational condition of the device and controls a presentation of said operational condition.

According to the invention operational conditions which are defined as not allowed may be presented as an error indication. Further according to the invention at least one of the signal generators may be an active generator generating electric signals.

According to an embodiment of the invention the circuit may comprise a storage in which is stored the signal patterns for all allowed conditions of the device, the signals from the signal generators are frequently compared with the stored signal patterns, and if the signal pattern is not found among the allowed patterns an error indication is made.

An error may be indicated by switching off the presentation of the operational condition of the device.

The allowed signal patterns are such patterns which occur during normal not faulty use of the device. Say that the device has a dose setting wheel which is covered by the protective cap when this cap is mounted on the device. In that case a pattern of signals comprising a signal indicating that the cap is on and another signal indicating that the dose setting wheel is operated will not be allowed as the dose setting wheel may not be operated when it is covered by the cap as this represent an obvious logical discrepancy. If locks are provided by which it is intended to exclude concomitant operation of two of the elements of the syringe, then signals indicating that these two elements are nevertheless operated concomitantly will cause an indication of error.

In an embodiment of the device according to the invention the circuit may be designed to count the number of signals send from each of the signal generators, to compare these numbers with set values stored in the circuit, and to give off a signal when one of the numbers exceed the set value for the signal generator in question, which signal provokes an error indication. By this feature it may be ensured that the device is only used for a number of operations and that the device is replaced by a new one before dysfunction due to wear becomes probable.

If a switch is worn to an extent which makes its stability questionable this will be manifested by the fact that the switch appears as off when it should be on or vice versa which soon will lead to a not allowed signal pattern. When this pattern is detected as not being among the allowed patterns the circuit will turn off the electronic presentation of parameters and the device is made not useable.

As a not allowed signal pattern may be induced by an event which is not related to the condition of the device, e.g. a transient electromagnetic field caused by any electric apparatus in the vicinity, the circuit may, when it turns off the electronic presentation, be reset to allow this presentation again. If the turning off of the electronic presentation is due to an event outside the device, the device will be usable again after the resetting but if the not allowed signal pattern was caused by a failing switch, this switch will soon fail again and turn off the electronic presentation.

Another check of the function may be obtained by summing up the number of doses injected since the ampoule was changed. If the accumulated dose exceeds the total content in a new ampoule an error is reported, e.g. by turning off the electronic presentation.

Recognizing that the switches and generators have a greatly enhanced probability of failing when they have been used a number of times the circuit may be designed to count the number of signals sent from each of the signal generators, to compare these numbers with set values stored in the circuit, and to give off a signal when one of the numbers exceed the set value for the signal generator in question, which signal forms a part of the signal pattern representing the condition of the device and makes this a not allowed pattern. Consequently it causes the device to be disabled when the counts for one of the signal generators reach the number set for that generator.

As the disabling of the device on the basis of the counting of signals from the signal generators is predictable, a warning may be presented to the user when one of the generators has produced a number of signals near the set number for this generator. In this way the user may avoid the inconvenience of a suddenly failing device.

To further avoid sudden failing of the device, the battery condition is currently monitored and a low battery is indicated some time before the battery is totally exhausted.

The failing of the switches and generators may not be foreseen and will cause a sudden disabling of the device. For emergency the circuit may then be reset and the device may be used a few times more unless the switches have become so unstable that the device is at once disabled again.

In the following an embodiment of the invention is described with references to the drawing in which FIG. 1 shows schematically an injection device with electrical signal generators FIG. 2 a graph showing how operations brings an injection device according to the invention from one condition to another.

The device in FIG. 1 comprises the following operative members:

a dose setting wheel 4 by the turning of which a dose may be set an injection button 5 a cartridge holder and a cartridge 2 accommodated in a housing 1 a removable protective cap 8 covering the dose setting wheel 4 and the cartridge holder 3.

Further the following mechanical locks are established:

when button 5 is pressed home it is locked in this position. The button 5 is released when the dose setting wheel 4 is operated. Consequently the button 5 cannot be in its pressed home position during setting of a dose; if the button 5 is maintained in its pressed home position, the dose setting wheel 4 cannot be turned. The correct function of the lock is checked by the electronics as previously explained by interpreting a signal indicating an operation which should be locked as not allowed.

the dose setting wheel 4 is locked when the cartridge holder 3 is open. This locking is appropriate as the opening of the cartridge holder 3 as a rule is performed to change the cartridge 2. During the changing of the cartridge 2 a piston rod, through which a movement corresponding to the set dose is transferred to a piston in the cartridge when the button 5 is pressed home, have to be moved backward to make space for the new full cartridge and consequently the coupling between the dose setting mechanism and the piston rod is released to make the piston rod freely movable. When said coupling is released a turning of the dose setting wheel 4 will activate the generator coupled to said wheel and make the user think that he sets a dose, but due to the released coupling no dose or a wrong dose will be injected by the operation of the button 5. To avoid such a malfunction the said mechanic lock is established. Also by this lock the correct function is checked by the electronics by interpreting a signal indicating an operation which should be locked as not allowed.

When a dose is set it may be injected by pressing the button 5. The injection takes place through a needle 6 which can be mounted on the syringe by a needle hub 7 carrying the needle.

The button 5, the cartridge holder 3, and the cap 8 are each collaborating with a switch indicated by the points 13, 12 and 11, respectively. Each switch has two positions, ON or OFF, so that the position of the switch is representative for the condition of the element collaborating with the switch in question. These conditions are:

The cap on or off the button down (pressed home) or up (not pressed home)

the lid closed or not closed (open)

The eight conditions defined by the positions of the above mentioned three switches are shown in table I.

Turning of the dose setting wheel 4 will result in signals from a signal generator 14 cooperating with the dose setting wheel to give off a number of pulses corresponding to the extent of the turning of the wheel and having a polarity by which it is indicated whether the turning of the wheel 4 results in an increase or a decrease of the number of set units.

TABLE I

| Condition | I | II | III | IV | V | VI | VII | VIII |
|---|---|---|---|---|---|---|---|---|
| Cap | on | on | on | on | off | off | off | off |
| Button | down | down | up | up | down | down | up | up |
| Cartridge Holder | open | clsd | open | clsd | open | clsd | open | clsd |
| Allowed | − | + | − | + | + | + | + | + |
| Dose sett. | − | − | − | − | − | − | − | + |

As it is seen from table I the conditions I and III are not allowed because the cartridge holder cannot be open when the cap is on.

In the conditions allowed for the switches dose setting signals may only be accepted in condition VIII. With the switches in condition I-IV the dose setting wheel 4 cannot be operated because the cap 8 is on. In condition V and VI the dose setting wheel may not be operated because the button 5 is in its home pressed position; if a dose setting signal is nevertheless received by the circuit it will indicate malfunction of the lock locking the dose setting wheel when the button is down.

A dose setting signal when the switches are in condition VII will indicate malfunction of the locking of the dose setting wheel when the lid is open.

The switches may each serve a purpose of its own. The cap on/off switch 11 may switch off a display to save battery when the cap is on. Further the activation of the switch 11 when the cap is demounted may start a display test by which all segments in the display are shortly activated to allow the user to know if all the segments are operational. The button down/up switch 13 may indicate when the button is pressed home and a injection has been completed, if the button is not fully pressed home the injection is not completed and the set dose has not been injected. Further this switch may reset and start a stop watch indicating the time passed since the latest injection.

The cartridge holder open/closed switch 12 indicates the possible change of cartridge and deletes a set dose from the electronic presentation, e.g. a display, as a cartridge shifting procedure ensuring that the piston rod abuts the piston of the new cartridge has to be performed before a dose can be set. The opening and closing of the cartridge holder also may reset a possible malfunction reaction of the circuit to make the device function again if the malfunction reaction was due to an environmental event, e.g. a transient electromagnetic field, whereas the malfunction reaction will soon occur again if it was due to malfunction of the device itself.

Figure 2:
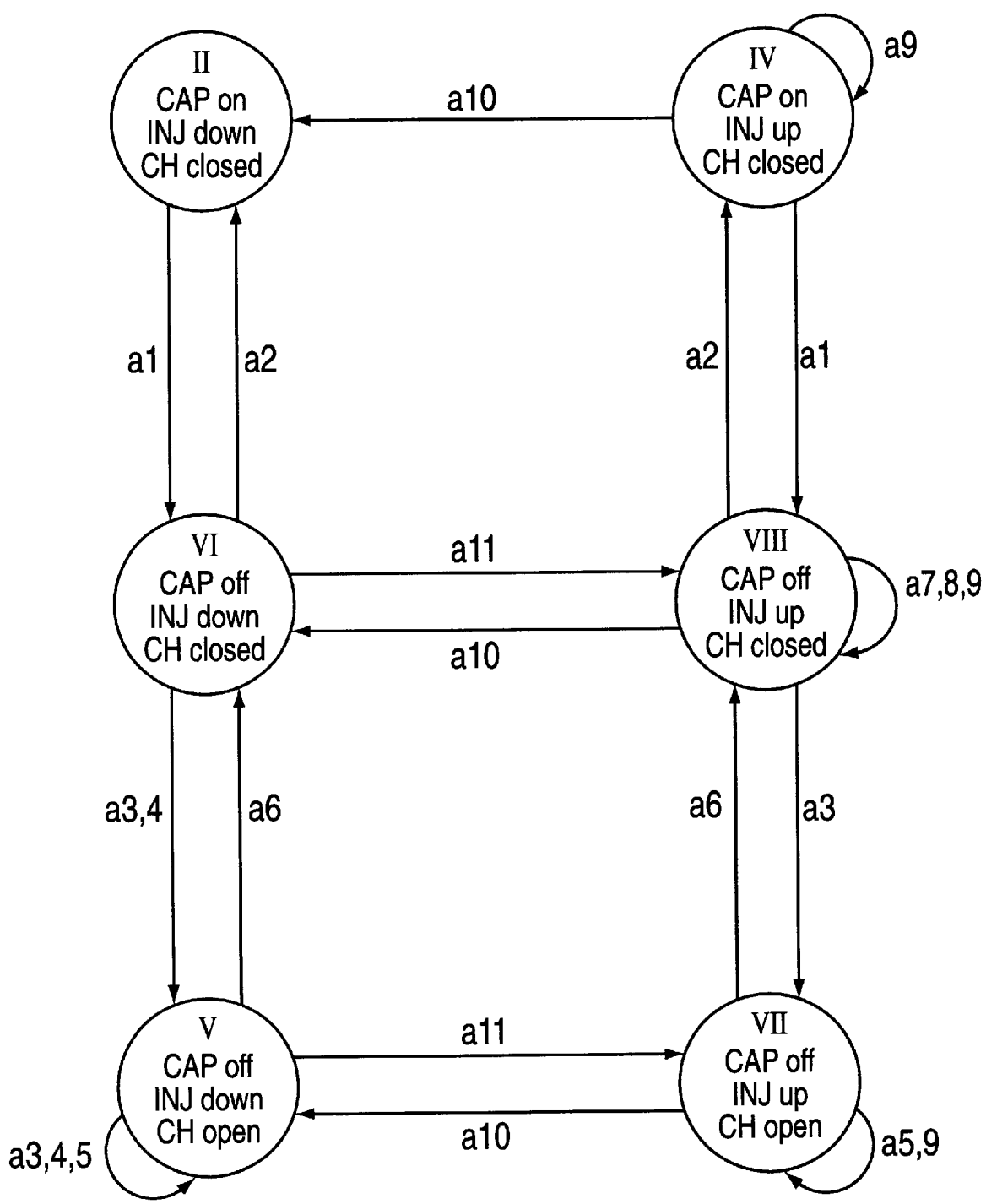

The following actions may be performed a₁ The cap may be removed a₂ The cap may be replaced a_3 The cartridge holder may be opened partially
a_4 The cartridge holder may be opened fully
a_5 The cartridge holder may be closed partly
a_6 The cartridge holder may be closed fully
a_7 The setting of the dose may be increased
a_8 The setting of the dose may be decreased
a_9 The injection button may be partly depressed or released
a_10 The injection button may be fully depressed
a_11 The injection button may be released In FIG. 2 it is illustrated how the actions either leave the switches unchanged or bring them from one of their six allowed combinations to another. In FIG. 2, the injection button is designated "INJ" and the cartridge holder is designated "CH".

When the device is stored in condition II with the cap on, only one transaction is possible; the cap may be removed, a,, which will bring the device to condition VI. From condition VI the device may either be brought back to condition II by remounting the cap, a_2, or it may be brought into condition V by opening the cartridge holder partially or fully, transactions a_3 or a_4, respectively, or into condition VIII by releasing the injection button, a_11.

It shall be noticed that the descriptions of the conditions of the cap 8, cartridge holder 3, and button 5 are
1. The cap on or not on
2. The cartridge holder closed or not closed
3. The button fully depressed or not fully depressed.

This may be interpreted so that when the cap is only almost on it is OFF, when the cartridge holder is not fully closed it is OPEN, and when the button is not fully depressed it is UP.

In condition V the cartridge holder may be opened or closed more or less, as long as it is not fully closed the device remains in condition V. In the same way the device remains in condition VII as long as the cartridge holder is not fully closed, a_6, or the injection button is not fully depressed, a_10.

Due to the provision of a mechanical lock the dose setting can only be performed when the device is in condition VIII and consequently operation of the dose setting wheel should not bring the device out of condition VIII. If dose setting signals are received with the switches in another condition it is interpreted as an indication of malfunction.

It shall be noticed that in other embodiments of the device other locks and switches may be provided controlling other functions of the syringe. E.g. in a preferred embodiment the condition VII is made a not allowed condition by the provision of a lock which prevent the cartridge holder from being opened when the button is up and correspondingly prevent the button from coming up when the cartridge holder is open. To illustrate the possible conditions of such an embodiment not only condition VII, but also the transactions a_3 and a_11 leading to this condition and the transactions a_6 and a_10 leading away from condition VII to the conditions VIII and V, respectively, should be deleted in FIG. 2.

What is claimed is:

1. An injection device comprising:
   a plurality of operative elements for setting and injecting of set doses of medicine;
   signal generators connected to at least two of said operative elements to generate output signals representing operating conditions of said at least two operative elements, wherein the operating conditions indicated by such output signals individually are not indicative of whether an error state exists; and
   an electronic circuit coupled to said signal generators for receiving said output signals and for determining whether the combination of said output signals indicates an error state for said device.

2. A device according to claim 1, wherein said electronic circuit further comprises means for generating an error signal responsive to identifying an error state.

3. A device according to claim 2, wherein said electronic circuit comprises a storage device containing all combinations of input signals which correspond to non-error states of said device, and a device for comparing said output signals with said stored combinations on a relatively frequent basis to detect the presence of error states.

4. A device according to claim 3, wherein said electronic circuit includes a circuit for counting the number of signals sent from each signal generator, a circuit for comparing such numbers with stored values, and a circuit generating a signal when a number exceeds its corresponding stored value.

5. A device according to claim 1, wherein at least one of said signal generators includes an electric switch having on and off positions.

6. A device according to claim 5, wherein at least one of said signal generators is an active generator.

7. A device according to claim 1, wherein at least one of said signal generators is an active generator.

8. A device according to claim 1, wherein said device further includes a means for generating an external presentation of the operating condition of the device and for switching off such external presentation when an error condition is detected.

9. A device according to claim 8, further including a means for resetting the means for switching off such external presentation.

10. A device according to claim 1, wherein said operative elements include a dose-setting device and an injection button and wherein said device includes a signal generator associated with each of said dose-setting device and said injection button.

11. A device according to claim 10, wherein said device includes a housing and said operative elements further include a protective cap, which can selectively be mounted on said housing, and a cartridge holder which can selectively be disengaged from said housing for changing cartridges, and said device includes a signal generator for detecting whether said cap is mounted on said housing and a signal generator for detecting when said cartridge holder is disengaged from said housing.

12. An injection device comprising a housing, a dose-setting wheel rotatably supported by said housing for setting an injection dose, an injection button supported by said housing and moveable between a plurality of first positions, corresponding to selected doses, and a second position for injecting the selected dose, a first signal generator connected to said dose-setting wheel for generating a first output signal in response to rotation of said wheel, a second signal generator for generating a second output signal indicative of whether said injection button is in said second position or one of said first positions, and an electronic circuit coupled to said signal generators for receiving said output signals and for comparing said output signals with one another to determine whether the combination of said output signals indicate an error state for said device.

13. A device according to claim 12, further comprising a cartridge holder which can be selectively mounted on said housing for holding a cartridge containing a medicine, and a third signal generator for generating a third output signal indicative of whether said cartridge holder is mounted on said housing, wherein said electronic circuit receives said third output signal and determines whether the combination of said first, second, and third output signals indicates an error state.

14. A device according to claim 13, further comprising a cap selectively mountable on said housing for selectively covering the cartridge holder, and a fourth signal generator for generating a fourth output signal indicative of whether the cap is mounted on the housing, and wherein said electronic circuit receives said fourth output signal for determining whether said fourth output signal, in combination with said first, second, and third output signals, indicates an error state.

15. An injection device comprising a housing, a dose-setting wheel rotatably supported by said housing for setting an injection dose, an injection button supported by said housing and moveable between a plurality of first positions, corresponding to selected doses, and a second position for injecting the selected dose, a first signal generator connected to said dose-setting wheel for generating a first output signal in response to rotation of said wheel, a second signal generator for generating a second output signal indicative of whether said injection button is in said second position or one of said first positions, and an electronic circuit coupled to said signal generators for storing a number value for each generator representing the predetermined maximum desired use of said device, for receiving and counting the number of signals from each generator, and for generating a signal when the number of signals exceeds a corresponding stored value for said generator.

16. A device according to claim 15, further comprising a cartridge holder which can be selectively mounted on said housing for holding a cartridge containing a medicine, and a third signal generator for generating a third output signal indicative of whether said cartridge holder is mounted on said housing, wherein said electronic circuit receives and counts the number of said third output signals and generates a signal when such number exceeds a corresponding stored value for said third signal generator.

17. A device according to claim 16, further comprising a cap selectively mountable on said housing for selectively covering the cartridge holder, and a fourth signal generator for generating a fourth output signal indicative of whether the cap is mounted on the housing, and wherein said electronic circuit receives and counts the number of said fourth output signals and generates a signal when the number of said fourth output signals exceeds a corresponding stored value for said fourth signal generator.

\* \* \* \* \*